United States Patent [19]

VandenBerg

[11] Patent Number: Plant 7,595

[45] Date of Patent: Jul. 16, 1991

[54] CHRYSANTHEMUM PLANT NAMED BRONZE COMET

[75] Inventor: Cornelis P. VandenBerg, Salinas, Calif.

[73] Assignee: Yoder Brothers, Inc., Barberton, Ohio

[21] Appl. No.: 435,817

[22] Filed: Nov. 14, 1989

[51] Int. Cl.[5] ..... A01H 5/00

[52] U.S. Cl. ..... Plt./79

[58] Field of Search ..... Plt./74, 76, 79; 800/200; 47/58

[56] References Cited

U.S. PATENT DOCUMENTS

P.P. 5,809 11/1986 Duffett ..... Plt./76

4,616,099 10/1986 Sparkes ..... 47/58

OTHER PUBLICATIONS

Searle, S. A., et al., "Breeding and Selection"; Appendix I, *Chrysanthemums the Year Round*, Blandford Press, London, 1968, pp. 26–29, 320–327.

Gosling, S. G., "Appendix II Sporting and Irradiation", *The Chrysanthemum Manual*, Nat. Chrysanth. Soc., London, 1979, pp. 329–336.

*Primary Examiner*—James R. Feyrer

*Attorney, Agent, or Firm*—Foley & Lardner

[57] ABSTRACT

A Chrysanthemum plant named Bronze Comet particularly characterized by its flat to V-shaped capitulum form; quilled to spooned decorative capitulum type; bronze ray floret color; diameter across face of capitulum of up to 9 cm at maturity; uniform nine week photoperiodic flowering response to short days; medium plant height when grown as a single stem spray cut mum; and excellent tolerance to low temperatures for bud initiation and flower development.

1 Drawing Sheet

The present invention comprises a new and distinct cultivar of Chrysanthemum, botanically known as *Dendranthema grandiflora*, and referred to by the cultivar name Bronze Comet.

Bronze Comet, identified as 81-757B07, is a product of a mutation induction program which had the objective of creating new Chrysanthemum cultivars that would expand the color range of an existing cultivar while retaining all other traits.

Bronze Comet was discovered and selected by Cornelis P. VandenBerg on Sept. 18, 1985 in a controlled environment in Salinas, Calif. as one flowering plant within a flowering block established as rooted cuttings from stock plants which had been exposed as unrooted cuttings to an X-ray source of 1500 rads. The irradiated parent was the cultivar identified as Comet, disclosed in U.S. Plant Pat. No. 5,809.

The first act of asexual reproduction of Bronze Comet was accomplished when vegetative cuttings were taken from the initial selection in November 1985 in a controlled environment in Salinas, Calif., by technicians working under formulations established and supervised by Cornelis P. VandenBerg.

Horticultural examination of controlled flowerings of successive plantings has shown that the unique combination of characteristics as herein disclosed for Bronze Comet are firmly fixed and are retained through successive generations of asexual reproduction.

Bronze Comet has not been observed under all possible environmental conditions. The phenotype may vary significantly with variations in environment such as temperature, light intensity and daylength.

The following observations, measurements and comparisons describe plants grown in Salinas, Calif. under greenhouse conditions which approximate those generally used in commercial greenhouse practice. The low temperature tolerance of the new variety as noted below was determined in repeated flowerings in Bogota, Colombia.

The following traits have been repeatedly observed and are determined to be basic characteristics of Bronze Comet, which, in combination, distinguish this Chrysanthemum as a new and distinct cultivar:

1. Flat to V-shaped capitulum form.
2. Quilled to spooned decorative capitulum type.
3. Bronze ray floret color.
4. Diameter across face of capitulum of up to 9 cm at maturity.
5. Uniform nine week photoperiodic flowering response to short days.
6. Peduncle length ranging from 15 to 25 cm on open, terminal sprays.
7. Medium plant height, requiring two long day weeks prior to short days to attain a flowered plant height of 90 to 100 cm for year-round flowerings.
8. Excellent tolerance to low temperatures for bud initiation and flower development.

The accompanying photographic drawing shows typical inflorescence and leaf characteristics of Bronze Comet, with the colors being as nearly true as possible with illustrations of this type. The color photograph is a perspective view of Bronze Comet grown as a single stem cut spray mum.

Of the commercial cultivars known to the inventor, the most similar in comparison to Bronze Comet is the parent cultivar Comet. All traits of Bronze Comet are similar to those of Comet, except the color of the ray florets. The color of the ray florets of Bronze Comet is bronze, while the color of Comet is described as purple.

In the following description color references are made to the Royal Horticultural Society Colour Chart. The color values were determined on plant material grown as a single stem cut spray mum in Salinas, Calif. on July 14, 1989.

Classification:

*Botanical.*—*Dendranthema grandiflora* cv Bronze Comet.

*Commercial.*—Quilled to spooned decorative cut spray mum.

INFLORESCENCE

A. Capitulum:

*Form.*—Flat to V-shaped.

*Type.*—Quilled to spooned decorative.

*Diameter across face.*—Up to 9 cm at maturity.

B. Corolla of ray florets:

*Color (general tonality from a distance of three meters).*—Bronze.

*Color (inner surface of tubular rays).*—163D heavily overlaid and streaked with 168B to 168C.

*Color (outer surface of tubular rays).*—163D slightly streaked with 173D.

*Shape.*—Outer rays are quilled, inner rays are spoon-tipped.

C. Corolla of disc florets:

*Color (mature).*—14B.

*Color (immature).*—Closest to 1A to 1B. Few disc florets. Number of disc florets depending on environmental conditions.

D. Reproductive organs:

*Androecium.*—Present on disc florets only; scant pollen.

*Gynoecium.*—Present on both ray and disc florets.

PLANT

A. General appearance:

*Height.*—Medium; 90 to 100 cm as a single stem cut mum with two long day weeks prior to short days.

B. Foliage:

*Color (upper surface).*—137A.

*Color (under surface).*—148B.

*Shape.*—Deeply lobed and serrated.

I claim:

1. A new and distinct Chrysanthemum plant named Bronze Comet, as described and illustrated.

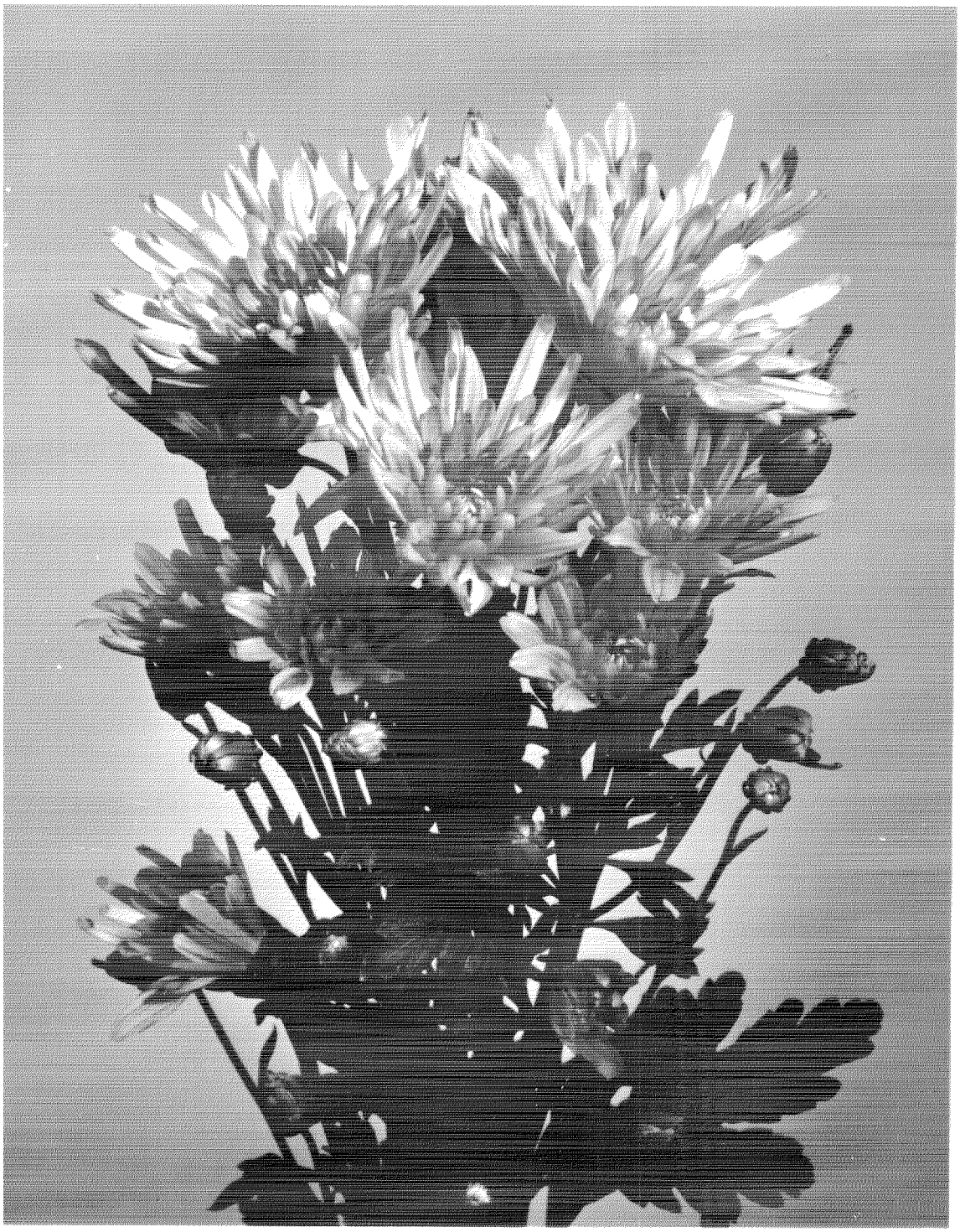

* * * * *